United States Patent [19]
Borden et al.

[11] Patent Number: 5,919,700
[45] Date of Patent: Jul. 6, 1999

[54] METHOD OF PROLIFERATING NATURAL KILLER CELLS WITH IL-16

[75] Inventors: Ernest C. Borden, Baltimore, Md.; Jonathan D'Cunha, Cedarburg, Wis.

[73] Assignee: MCW Research Foundation, Milwaukee, Wis.

[21] Appl. No.: 08/718,599

[22] Filed: Aug. 23, 1996

Related U.S. Application Data

[63] Continuation of application No. 08/329,911, Oct. 26, 1994, abandoned.

[51] Int. Cl.$^6$ .............................. C12N 5/00; C12N 5/06
[52] U.S. Cl. ...................... 435/372; 435/325; 435/372.3; 435/386; 424/93.7
[58] Field of Search ................................ 435/325, 375, 435/386, 372.3, 372; 424/93.7

[56] References Cited

U.S. PATENT DOCUMENTS

| | | | |
|---|---|---|---|
| 4,604,377 | 8/1986 | Fernandes et al. | 514/8 |
| 4,840,934 | 6/1989 | Anderson | 514/2 |
| 4,908,433 | 3/1990 | Mertelsmann et al. | 530/351 |
| 5,082,657 | 1/1992 | Ranson | 424/85.1 |
| 5,418,192 | 5/1995 | Borden et al. | 435/69.51 |

OTHER PUBLICATIONS

B. Korant., et al., #23 259 *J. Biol. Chem.* 14835–14839 (1984).
D. Blomstrom, et al., #19 261 *J. Biol. Chem.* 8811–8816 (1986).
N. Reich, et al., 84 *P.N.A.S. USA* 6394–9398 (Sept. 1987).
A Haas, et al., 262 #23 *J. Biol. Chem.* 11315–11323 (1987).
E. Knight, et al., 263 #10 *J. Biol. Chem.* 4520–4522 (1988).
E. Knight, Jr., et al., 8 *J. Interf. Res.*, Supp. 1, p. S4 (1988). #1–7 Abs.
N. Feltham, et al., 9 *J. Interf. Res.* 493–507 (1989).
H. Ziegler–Heitbrock, et al., 72 #1 *JNCI* 23–28 (Jan. 1984).
H. Ziegler–Heitbrock, et al., 46 *Can. Res.* 5947–5952 (Nov. 1986).
R. Philip, et al., 323 *Nature* 86–89 (Sep. 1986).
J. Nissen–Meyer, et al., 47 *Can. Res.* 2251–2258 (May 1987).
E. Borden, 54 #11 *Cancer* 2770–2776 (Dec. 1984). Supplement.
E. Borden, *Interferons And Cancer: How The Promise Is Being Kept*, "Interferons", vol. 5, Acad. Press 43–83 (1984). Ed. I. Gresser.
G. Antonelli, et al. "Generation of a Soluble IFN–Gamma Inducer by Oxidation of Galactose Residues on Macrophages" *Cell. Immun.* 94:440–446 (1985).
Y. Ozaki, et al. 144#3 *Biochem. Biophys. Res. Commun.* 1147–1153 (May 1987).
M. Julius, et al., 3 *Eur. J. Immunol.* 645–649 (1973).
M. Edelstein, et al., 143#9 *J. Immunol.* 2969–2973 (Nov. 1989).
J. Carlin, et al., 9 *J. IFN Res.* 167–173 (1989).
J. Carlin, et al., 139#7 *J. Immunol.* 2414–2418 (Oct. 1987).
J. Carlin, et al., 9 *J. IFN Res.* 329–337 (1989).
R. Devos, et al., 10#8 *Nuc. Acids Res.* 2487–2501 (1982).
J. Vilcek, "The Importance Of Having Gamma," in *Interferon 1982*, vol. 4, pp. 129–154 Academic Press (1982). Ed. I. Gresser.
Knight, Jr., et al., 263#10 *J. Biol. Chem.* 4520–4522 (Apr. 1988).
Recht, et al., 147#8 *J. Immunol.* 2617–2623 (Oct. 1991).
D'Cunha, et al., Abstract, *J. Immunol. Ther.* (Oct. 1992). vol. ?.
L. Moretta, et al., 55 *Adv. in Immun.* 341–381 (1994).
S. Rosenberg, Chapter 4 "Adoptive Immunotherapy of Cancer Using Lymphkine Activated Killer Cells and Recombinant Interleukin–2" in *Important Advances in Oncology*, Ed. DeVita, et al., Lippencott, Philadelphia, Pennsylvania pp. 55–91 (1986).
S. Rosenberg, et al., 313#23 *The New Eng. J. of Med.* 1485–1492 (1985).
L. Svedersky, et al., 133#2 *J. Immunol.* 714–718 (Aug. 1984).
L. Lanier, et al., 45 *FASEB* 2823–2828 (1986).
R. Foa, et al., 51 *Can. Res.* 964–968 (Feb. 1991).
R. Dillman, et al., 9#7 *J. Clin. Oncol.* 1233–1240 (Jul. 1991).

*Primary Examiner*—David M. Naff
*Assistant Examiner*—Janet M. Kerr
*Attorney, Agent, or Firm*—Quarles & Brady

[57] ABSTRACT

The invention relates to a method of stimulating the proliferation of natural killer cells with in vitro IL-16. A mixed lymphocyte cell population which contains natural killer cells can be nylon wool-purified, and cultured in the presence of an effective amount of IL-16 to stimulate the proliferation of natural killer cells. Effective concentrations of IL-16 which enhance the proliferation of natural killer cells range from 1 ng/ml to 1000 ng/ml. Both the full length IL-16 protein or the naturally occurring carboxy terminal-truncated form of IL-16 are suitable for stimulating the proliferation of the natural killer cells. The IL-16 induced proliferation results in at least a five-fold enrichment of natural killer cells, and the natural killer cells can be subsequently isolated from the mixed lymphocyte culture.

10 Claims, 4 Drawing Sheets

METHOD OF PROLIFERATING NATURAL KILLER CELLS WITH IL-16

This is a continuation of application Ser. No. 08/329,911 filed Oct. 26, 1994, now abandoned.

This invention relates to the uses of an interferon induced-protein, IL-16, to proliferate and stimulate lymphocyte cells. Specifically, the present invention relates to a method of using IL-16 to proliferate NK/LAK cells.

BACKGROUND OF THE INVENTION

The immune system protects the body from external and internal pathogens, such as bacteria, fungi, viruses, and cancer cells. T lymphocytes, B-lymphocytes (antibody producers), NK/LAK cells and macrophages (monocytes) are all components of the immune system.

T lymphocytes regulate the "cell mediated immunity" and function as helper cells, killer cells, or suppressor cells. Helper cells cooperate with B-lymphocytes for antibody production or for generating other T cell responses. Killer T cells eliminate virus-infected cells and cancer cells or reject foreign grafts. Suppressor T cells serve to modulate responses of other T cell classes.

T lymphocytes function as cells or through the release of soluble factors known as lymphokines or interleukins. In recent years, these functionally and biochemically unique soluble proteins have been discovered to play a central role in regulating the responsiveness of the immune system and/or act as antigen-non-specific effector molecules capable of mediating one or more aspects of immune function.

Cell interactions involved in cell mediated immunity require soluble helper or suppressor proteins. Most of these proteins are synthesized by hemopoietic cells, especially lymphoid cells and monocytes.

Lymphokines (interleukins) are mediators of these biological responses and regulate or affect both immune responses and other physiological systems. Biological characterization of lymphokines is still in a preliminary stage. This is primarily due to the small amount of lymphokines produced in in vitro systems. Lymphokines are active at extremely low physiologic concentrations.

IL-2 is one well-studied T lymphocyte and NK/LAK cell regulatory factor. Conditioned media from lectin-stimulated mononuclear cells was found to contain a mitogenic factor that supports the continuous exponential growth of lectin-activated human T cells and subsequently NK/LAK cells. It is now clear that IL-2 provides a mitogenic stimulus after lectin- or antigen-initiated T-cell activation or for NK or LAK cell activation. Since the discovery of IL-2, other T cell and NK cell activating lymphokines, such as IL-4, IL-6, and IL-12 have been identified. It is reasonable to postulate that there are other T and NK/LAK cell lymphocyte regulating lymphokines.

In other unrelated work, there has been considerable research with respect to a group of proteins known as interferons. See generally, Borden, E. C., "Interferons—Expanding therapeutic roles (Editorial)", *New Engl. J. Med.* 326:(22)1491–1493, 1992; Borden, E. C. "Interferons" in *Cancer Medicine*, Holland, J. F., et al. (Eds.), Lea & Febiger, pp 927–936, 1993; E. Borden, *Cancer* 54:2770–2776 (1984); E. Borden, *Interferons And Cancer: How The Promise Is Being Kept*, "Interferons", Vol. 5, Acad. Press, 43–83 (1984). The interferons are a family of proteins, each with distinct properties. For example, interferon α2 is most effective in treating cancers and interferon β is more effective for multiple sclerosis. Interferon γ has a role in immune regulation.

As a result of a large body of research on the interferons, it has become clear that they induce the synthesis of many new proteins within cells they contact. It is also believed that some of the many proteins induced by the interferons must somehow mediate the interferon-induced biological effects. However, the induced proteins' role in mediating the effects of interferons is not fully understood. See E. De Maeyer, et al., "Interferons And Other Regulatory Cytokines", John Wiley And Sons (1988).

One interferon-induced protein of about 15,000 daltons (157 amino acids) was isolated from the cytoplasm of a line of human lymphoblastoid cells after induction by interferons. In addition to the purification to homogeneity, the cloning and sequencing of the DNA and the amino acid sequence deduced from the cDNA have been reported. Particular portions of the gene responsible for transcription and the mechanism that hosts use to modify a 17-kDa precursor (about 165 amino acids) of the protein have also been defined. The 17-kDa protein differs from the secreted 15-kDa protein in that the 17-kDa protein has eight additional amino acids at the carboxy terminus. (The amino acid sequence of the 17-kDa protein, is disclosed below at SEQ ID NO:1.) See B. Korant, et al., *J. Bio. Chem.* 259:14835–14839 (1984); D. Blomstrom, et al., *J. Bio. Chem.* 261:8811–8816 (1986); N. Reich, et al., *P.N.A.S. USA* 84:6394–6398 (1987); E. Knight, et al., *J. Bio. Chem.* 263:4520–4522 (1988); N. Feltham, et al. *J. Interf. Res.* 9:493, 506 (1989).

We refer below to the 15-kDa protein as IL-16. (The 15-kDa secreted protein is referred to as DA15 and the 17-kDa precursor is referred to as DA17 in U.S. Ser. Nos.: 07/998,896, 07/590,565 and 07/486,473. The protein is referred to as "IL-15" in U.S. Ser. No: 08/086,529.)

SUMMARY OF THE INVENTION

We identify herein effects of IL-16 for the process of immune system activation and NK/LAK cell proliferation. In one embodiment, the present invention provides a process for activating and proliferating NK/LAK cells. This embodiment involves the step of exposing lymphocytes to a protein having the structure of IL-16, the protein having been produced outside of the host.

By "NK/LAK cells" we mean natural killer and lymphokine-activated killer cells. Both of these cell types have non-MHC restricted killing activity. NK cells are a subset of lymphocytes and are sometimes thought of as primitive CTLs that lack the specific T cell receptor for antigen recognition. The cells have the ability to lyse some tumor cells and normal cells infected by a virus and are not specific for particular viral antigenic determinants. NK cells are phenotypically characterized by the surface expression of low affinity receptors for IgG (Fcγ RIII or CD16) (D. Kraft, et al., *J. Immunol.* 133:180, 1984) and by the NCAM-homologous CD56 molecules (L. L. Lanier, et al., *J. Immunol.* 136:4480, 1986).

In an alternative embodiment, there is provided a composition for stimulating NK/LAK cells. This composition comprises an effective amount of a protein having the structure of IL-16. There is also provided a carrier that does not exceed pharmaceutically acceptable toxicity to the cells in the dosage that the composition delivers. In a preferred form, the carrier is a liquid, thus permitting injections.

It will be appreciated from the description above and the experiments described below that the inventors have discovered that IL-16 protein (and thus its precursor indirectly) stimulates NK/LAK cells to proliferate. This finding opens up important drug therapy uses for IL-16 (both in vitro and in vivo).

NK and LAK cells are both important cellular components of host response to malignant and viral diseases. These cells induce killing of a broader range of cellular targets than occurs with T cells. Murine NK and LAK cells can be shown to induce regression and cure mice of pulmonary metastases from various cancers. Destruction of tumor cells by activated NK and LAK cells can be demonstrated for human cells both in vitro and in vivo.

Adoptive cellular therapy with LAK cells activated by IL-2 occurs by in vitro incubation of cells derived from the peripheral blood of patients. IL-16 results in the same cellular activation as IL-2, as demonstrated below in the examples. After leukophoresis of patients for obtaining of a LAK cell population, harvested cells would be incubated for 1–7 (preferably 3–4) days in vitro with sufficient concentrations of IL-16. The cells would then be reinfused on single or multiple occasions into a patient bearing a tumor.

The cytokine network is comprised of many molecules with overlapping and complementary functions. The in vivo role of each molecule is likely linked to specific steps in immunological activation. IL-2 has been reported to induce or augment the activity of human NK and LAK cells. However, IL-2 alone is not sufficient to result in maximal proliferation and augmentation of NK and LAK cell cytotoxicity. Substantial evidence implicates other cytokines in this activity. (Borden and Sondel. *Cancer* 65:800–814, 1990.) One of these is IL-16. When combined with in vivo treatment, IL-2 has been effective in patients in yielding tumor regression. Proliferation of the in vitro LAK cell population for its expansion and activation as described in the previous paragraphs, would then be followed by treatment with IL-2, other cytokines, such as IL-16. A greater in vitro expansion of the number of LAK effector cells might be obtained either with IL-16 alone or with IL-16 in combination with other cytokines. In addition, IL-16 activated and expanded in vitro effector cells may prove more effective than those activated and expanded in IL-2. Potentially IL-16 expanded cells could then be further activated and proliferated in vivo by administration of IL-16, IL-2 or other cytokines which expand and activate tumor cell populations.

It is advantageous if the proteins that activate NK/LAK are exocellular proteins. It is known that IL-16 is naturally released from the cell into the surrounding medium, where it acts to modulate immune cell function.

The objects of the invention include:

(a) activating and inducing proliferation of NK/LAK cells;

(b) providing processes for stimulating host defense mechanism activity of NK/LAK cells; and (c) providing compositions useful in connection with such processes.

These and other objects and advantages of the present invention will be apparent from the description which follows. The following embodiments do not represent the full scope of the invention. Rather, the invention may be employed in other embodiments. Reference is therefore to be made to the claims herein for interpreting the scope of the present invention.

DESCRIPTION OF THE INVENTION

Interferons (IFNs) are proteins that mediate important intercellular regulatory functions and elicit multiple biological responses in cultured cells, animals, and humans. Although molecular mechanisms underlying these biologic responses remain largely unknown, it is thought that they are mediated by the regulated synthesis of induced proteins (M. Revel, et al., *TIBS* 166:11, 1986). One of these induced proteins, a 15-kDa protein (IL-16), is synthesized in mammalian cells as a 17-kDa precursor (pre-IL-16) after treatment with IFN-α or IFN-β (B. D. Korant, et al., *J. Biol. Chem.* 259:14385, 1984). This precursor is processed by cellular converting enzyme, cleaving the eight carboxyl-terminal amino acids yielding a 157 amino acid mature 15-kDa protein that is secreted by monocytes and lymphocytes (N. Feltham, et al., *J. Interferon Res.* 9:493, 1989; E. Knight Jr., et al., *J. Immunol.* 146:2280, 1991). Recht, et al. has shown that both native and recombinant IL-16 induce the synthesis and secretion of IFN-γ from B cell-depleted lymphocytes (M. Recht, et al., *J. Immunol.* 147:2617, 1992).

Because many of the activities evoked by cytokines are likely linked to activating a specific biological response, we examined the immunomodulatory effects of IL-16 to further define what role it might play in intercellular signaling.

We found that exposure of a lymphocyte population to IL-16 resulted in a specific enhancement of the NK/LAK cell population.

The present invention is therefore a method of proliferating NK/LAK cells. The method involves exposure of a lymphocyte cell population to a protein with the structure of IL-16. By "lymphocyte cell population" we mean a population of cells that include peripheral blood mononuclear cells. Preferably, the lymphocyte cell population has been depleted of B cells. Most preferably, the lymphocyte cell population is comprised of nylon wool non-adherent peripheral blood lymphocytes (PBLs) which are phenotypically 80–85% CD3+, 5–8% CD16+, less than 2% CD14+, and less than 2% CD19+.

The Examples below demonstrate a preferred method of isolating PBLs suitable for the present invention. In general, a PBL cell population of between $10^5$ and $10^7$ cells per ml are placed in a suitable receptacle, such as a round bottomed microtiter dish or a cell culture flask, and exposed to IL-16. This exposure is preferably by applying the IL-16 in a liquid solution at a concentration of between 1 ng/ml and 1000 ng/ml to the lymphocytes and incubating at 37° C. for 1–7 days. Most preferably, the IL-16 is at a concentration between 50 ng/ml and 500 ng/ml.

NK/LAK cell proliferation is preferably measured as described below in the section entitled "Cell Proliferation Assays." By "proliferation" we mean that the population of NK/LAK cells within the lymphocyte cell population has at least doubled. Preferably, the NK/LAK cell population has increased at least five-fold. Most preferably, the NK/LAK cell population has increased at least 13-fold.

The Examples below demonstrate that IL-16 concentrations of between 1 and 1000 ng/ml will cause cell proliferation.

The method of the present invention is envisioned to also successfully cause NK/LAK cells to proliferate in vivo. We envision that IL-16 will be administered subcutaneously, intramuscularly or intravenously one or several times a day.

The present invention is also a composition causing proliferation of an NK/LAK cell. This composition comprises an effective amount of a protein having the structure of IL-16 and a carrier which does not exceed pharmaceutically acceptable toxicity to the cells. In the Examples below, the carrier is buffered saline in tissue culture medium. Another suitable carrier for in vitro usage would be sterile water.

Acceptable carriers for in vivo usage would be sterile water, buffered saline or ethylene glycol.

The Examples below describe how to obtain a preparation of IL-16. A preferred plasmid capable of expressing IL-16 has been deposited as ATCC 68216 on Feb. 8, 1990, at the American Type Culture Collection, Rockville, Md., U.S.A., under Budapest Treaty conditions. These cultures will be made available as required by applicable patent law. Such availability is not intended as a license. The IL-16 strain is designated as E. coli C-600, pBR322-TRP-IFN-15 kDa and E. coli BL-21 and can be expressed using conventional techniques.

In the alternative, IL-16 can be isolated from cells as described in D. Blomstrum, J. Biol. Chem. 261:8811–8816 (1986); B. Korant, et al., J. Biol. Chem. 259:14835–14839 (1984); and N. Feltham, et al., J. Interf. Res. 9:493–507 (1989).

It is known to one of skill in the art of molecular biology that small mutations, deletions and additions to an amino acid sequence can result in no loss of enzymatic activity. We envision that even after minor modifications, the IL-16 structure would still be suitable for the present invention. Therefore, by "protein having the structure of IL-16," we mean both the sequence of SEQ ID NO:1 and the sequence of SEQ ID NO:1 with minor mutations, deletions or additions. While the Examples described below were performed with IL-16 of native sequence, one could easily determine whether an altered IL-16 was suitable for the present invention by performing the cell proliferation assay described below with the altered IL-16. An increase in NK-LAK cells of at least two-fold indicates that the slight alteration or mutation has not substantially changed the IL-16 activity.

EXAMPLES

1. Materials and Methods

PBL Cell Preparation

Heparinized venous blood was drawn from normal donors and separated via density gradient centrifugation on Histopaque (Sigma Chemical Co., St. Louis, Mo., specific density 1.077 g/ml) centrifuged at 500×g. PBMCs were washed once with DPBS ($Ca^{+2}$ and $Mg^{+2}$ free) and washed once in RPMI 1640 (Sigma) containing 28.8 mM $NaHCO_3$ and 27.8 mM HEPES supplemented with 10% FCS (Hyclone, Logan, UT), 2 mM L-glutamine (Sigma), and 50 μl/ml gentamicin (Sigma) (cRPMI). T lymphocytes were purified by concentrating the cells to a total volume of 2 ml cRPMI and adding to scrubbed, nylon wool for 60 min at 37° C. Nylon nonadherent cells were extensively washed with cRPMI. Nylon wool purified lymphocytes phenotypically were >85% CD3+ and >10% CD16+, while being <5% CD14+ and <2% CD19% by FACS analysis.

Cytokines and Lectins

Human rIL-2 ($2\times10^7$ U/mg) (Hoffmann-LaRoche) was obtained commercially. Human rIFN-γ ($2\times10^7$ U/mg) was a gift of Biogen Corp., Cambridge, Mass.

Antibodies

A polyclonal antiserum to homogenous IL-16 purified from the cytoplasms of IFN-β-treated Daudi cells was raised in an NZW rabbit as previously described in Knight, et al., Jour. Biol. Chem. 263[10]:4520–4522, 1988.

Monoclonal antibodies (mAb) used in flow cytometry for determination of cell surface Ag were purchased from Becton Dickinson, Mountain View, Calif. They included: Leu-2a (CD8), Leu-3a (CD4), Leu-4 (CD3), Leu-11c (CD16), Leu-16 (CD20), Leu-19 (CD56), and Leu-M3 (CD14). All were used at the recommended concentrations.

Recombinant IL-16 Preparation

IL-16 was prepared as described by a modification of the process described by Loeb and Haas (Loeb, et al., Journal of Biological Chemistry 267, 7806–7813, 1992, incorporated by reference as if fully set forth below). Briefly, cultures of E. coli containing the IL-16 expression plasmid were grown and expression was induced with IPTG. All subsequent steps were performed at 4° C. Bacteria were lysed in a French pressure cell at 16,000 p.s.i. and centrifuged for 90 min at $10^5 \times g$. Supernatant proteins precipitating between 30% and 50% saturated ammonium sulfate were then dialyzed, and IL-16 was purified by sequential chromatography on DEAE-52 cellulose (Whatman), HR 5/5 phenyl-SEPHAROSE fast protein liquid chromatography column (Pharmacia LKB Biotechnology Inc.), and HR 10/30 SUPEROSE 12 gel exclusion fast protein liquid chromatography column (Pharmacia LKB Biotechnology Inc.). Protein concentration of IL-16 was determined spectrophotometrically and purity by SDS-PAGE. The protein was stored in concentrations ranging from 0.31 mg/ml to 1.5 mg/ml in $H_2O$, 1 mM DTT, 0.01% sodium azide at 4° C.

Cell Proliferation Assays

Nylon wool purified lymphocytes (PBLs) ($10^6$ cells/ml) were cultured in a final volume of 100 μl cRPMI in triplicate in round-bottomed 96-well plates (Costar, Cambridge, Mass.). The cells were mixed with various concentrations (between 1 ng/ml and 1000 ng/ml) of IL-16. Cultures were incubated (37° C., 5% $CO_2$) for 72 hours and pulsed for 12 hours with [$^3$H]-thymidine (1.0 uCi, New England nuclear, Boston, Mass.). Cells were then harvested onto glass fiber filters and assayed for radioactivity by liquid scintillation counting.

Immunophenotyping

Analysis of cell surface antigens on peripheral blood lymphocytes was done by two-color immunofluorescent flow cytometry using standard direct staining methods (Truitt et al, J. Immunotherapy: 274,1992). The cells were washed once using Flow Staining Buffer (FSB) (DPBS +0.1% $NaN_3$, resuspended at $2\times10^6$ cells/ml, and aliquots of 100 μl were stained with the appropriate concentration (based on manufacturer's suggestions) of fluorescein isothiocyanate (FITC)—conjugated and phycoerythrin (PE)—conjugated mouse monoclonal antibodies (Becton Dickinson, San Jose, Calif.) for 30 minutes at 4° C. The cells were then washed twice with FSB, resuspended in 500 μl FSB, and the labeled cells were analyzed on a FACS Analyzer (Becton Dickinson) equipped with a FACSLite laser and CONSORT 30 computer support. Antigenic specificities of the monoclonal antibodies (mAb) included the following: CD3 (pan T cell marker), CD4 (T helper marker), CD8 (cytotoxic T cell marker), CD14 (monocyte marker), CD16 (NK cell marker, FcγRIII receptor), CD19 (B cell marker), CD25 (IL-2 receptor α chain), CD56 (NK cell marker), and HLA-DR (MHC class II antigen). Results are reported as percent positive cells after subtraction of values for non-specific isotype controls (FITC-IgG2a and PE-IgG2a).

Cell-mediated lympholysis (CML) assays

NK/LAK was evaluated using chromium-release CML assays (Grimm et al, J. Exp. Med. 155: 1823, 1982; Truitt et al, J. Immunotherapy 11: 274, 1992). Effector PBLs were serially diluted in 96-well V-bottom microwell plates using RPXI+10% FBS. The target cells were labeled with $^{51}$Cr as sodium chromate for 1 hour at 37° C., washed 3 times, diluted to the appropriate concentration, and added to microwells (5,000 targets/well). Effector (E): target (T) ratios ranging from 100:1 to 0.8:1 were then assayed in triplicate wells in a final volume of 150 μl. After centrifugation, microplates were incubated for 3 hours at 37° C. 100 μl of supernatant was then removed for measurement of $^{51}$Cr release. Maximum $^{51}$Cr release and spontaneous values were determined from six wells containing labeled target cells and 2.5% "7X" detergent (LINBRO, McLean, Va.) or medium, respectively. Spontaneous $^{51}$Cr-release was <10% of maximum release. The percentage of specific $^{51}$Cr release was calculated from the mean CPM values of triplicate wells as follows: 100 (CPM experimental—CPM spontaneous release)/(CPM maximum release—CPM spontaneous release). $^{51}$Cr release data were converted to lytic units (LU) with one LU defined as the number of effectors resulting in 30% of maximum specific $^{51}$Cr release from 5,000 target cells. To assess NK activity, K562, an NK-sensitive, LAK-sensitive erythroleukemia cell line was used as a target cell. To assess LAK cell activity, Daudi, a LAK-sensitive, NK-resistant Burkitt's lymphoma cell line, was used as a target in the CML.

Immunomagnetic separation of CD3+T-cells and CD56+NK cells

CD56+NK cells were separated from CD3+T-cells by the use of a commercially available NK isolation kit (Miltenyi Biotec, Inc., Sunnyvale, Calif.) which isolates NK cells by negative enrichment. For a typical experiment, $10^8$ PBLs were resuspended in 500 μl MACS buffer (MB) (DPBS/0.5% BSA) and 100 μl Reagent A (a cocktail of modified CD3, CD4, CD19, and CD33 mouse IgG1 isotype antibodies) and incubated at 4° C. for 30 minutes. The cells are then washed and resuspended in 500 μl MB and 100 μl Reagent B (colloidal superparamagnetic MACS microbeads recognizing reagent A) and incubated at 4° C. for 30 minutes. The cells are then washed and resuspended in 500 μl MB. This solution is then applied to a B2 MACS column (maximum capacity of $10^8$ cells) in a MACS separator that was pre-equilibrated and pre-cooled with MB. The effluent was then collected in a volume of 5 mls using a 22 gauge needle for flow regulation. This effluent was repassed over the column and 10 MLS was collected (designated NK fraction). The column was removed from the magnetic field, cells flushed up, returned to the magnetic field, and washed with 12 mls of MB (designated was fraction) using a 20 g needle for a flow regulation. The column was again removed from the magnetic field, cells flushed up, and washed with 10–15 mls of MB (designated T cell fraction). The three fractions were then pelleted by centrifugation, resuspended in RPMI+10% AB serum, and counted. Typical yields and purity (assessed by flow cytometry) were as follows: 2×10$^6$ cells in NK fraction (65–75% CD56+CD3−,<1% CD3+ CD56−), 5×10$^5$ cells in wash fraction (40–50% CD3+, 40–50% CD56+), and 5×10$^7$ cells in T cell fraction (90–95% CD3+CD56−,<2% CD56+CD3−).

Detection of cytokines by immunoassay

PBLs ($10^7$ cells/ml) were cultured with or without activating agents and cell-free supernatants were prepared at various timepoints, frozen at −80° C., and assayed using commercially available kits. IFN-γ was detected by radioimmunoassay (Centocor Corp., Malvern, Pa.) with a sensitivity of 0.1 U/ml. IL-2 and IL-12 were detected by ELISA (R+D Systems, Inc., Minneapolis, Minn.) with sensitivities of 6 pg/ml (IL-2) and 5 pg/ML (IL-12).

Isolation of total RNA

Total RNA was isolated by a modified single-step guanidinium-thiocyanatephenol method. Cells were centrifuged at 12,000× g for 1 minute and washed with DPBS. The cell pellet is then solubilized in 1.5 mls of RNAzol B (tel-test Inc., Friendswood, Tex.) and 0.15 ml CHCl$_3$, shaken vigorously and placed on ice for 15 minutes. The suspension is then centrifuged at 12,000× g for 15 minutes. The upper phase was then removed and an equal volume of isopropanol was added and placed at −80° C. overnight. The samples are then centrifuged at 12,000× g for 15 minutes, the pellet washed once with 75% EtOH, and resuspended in diethylpyrocarbonate (DEPC) treated H$_2$O.

Reverse-transcriptase PCB (RT-PCR)

RT-PCR was performed using a commercially available GeneAmp RNA PCR Kit (Perkin Elmer Cetus, Norwalk, Conn.) essentially as previously described (Kawasaki and Wang, 1989). 50 ng of total RNA was reverse transcribed into cDNA with murine leukemia virus reverse transcriptase using an oligo(dT) primer at 42° C. for 15 minutes. The entire reverse transcriptase reaction was subjected to 35 cycles of PCR (95° C. for 30 seconds, 60° C. for 1 minute, and 72° C. for 1 minute) using IFNγ- specific or G3PDH-specific primers (0.2 μM) (Clontech Laboratories, Inc., Palo Alto, Calif. ). The PCR reactions were then precipitated and the entire PCR product was separated by 1.5% agarose gel electrophoresis with visualization by ethidium bromide fluorescence.

2. Results

Since IL-16 induces the production of IFN-γ from lymphocytes, we were interested in determining whether IL-16 acts as a mitogen to lymphocytes. Recombinant human IL-16 was added to cultures of nylon wool non-adherent peripheral blood lymphocytes (PBLs) (80–85% CD3$^+$, 5–8% CD16$^+$,<2% CD14$^+$,<2% CD19$^+$) for 72 hours before radiolabeling with [$^3$H]thymidine ([$^3$H]-TdR) for 12 hours.

Figure 1A:
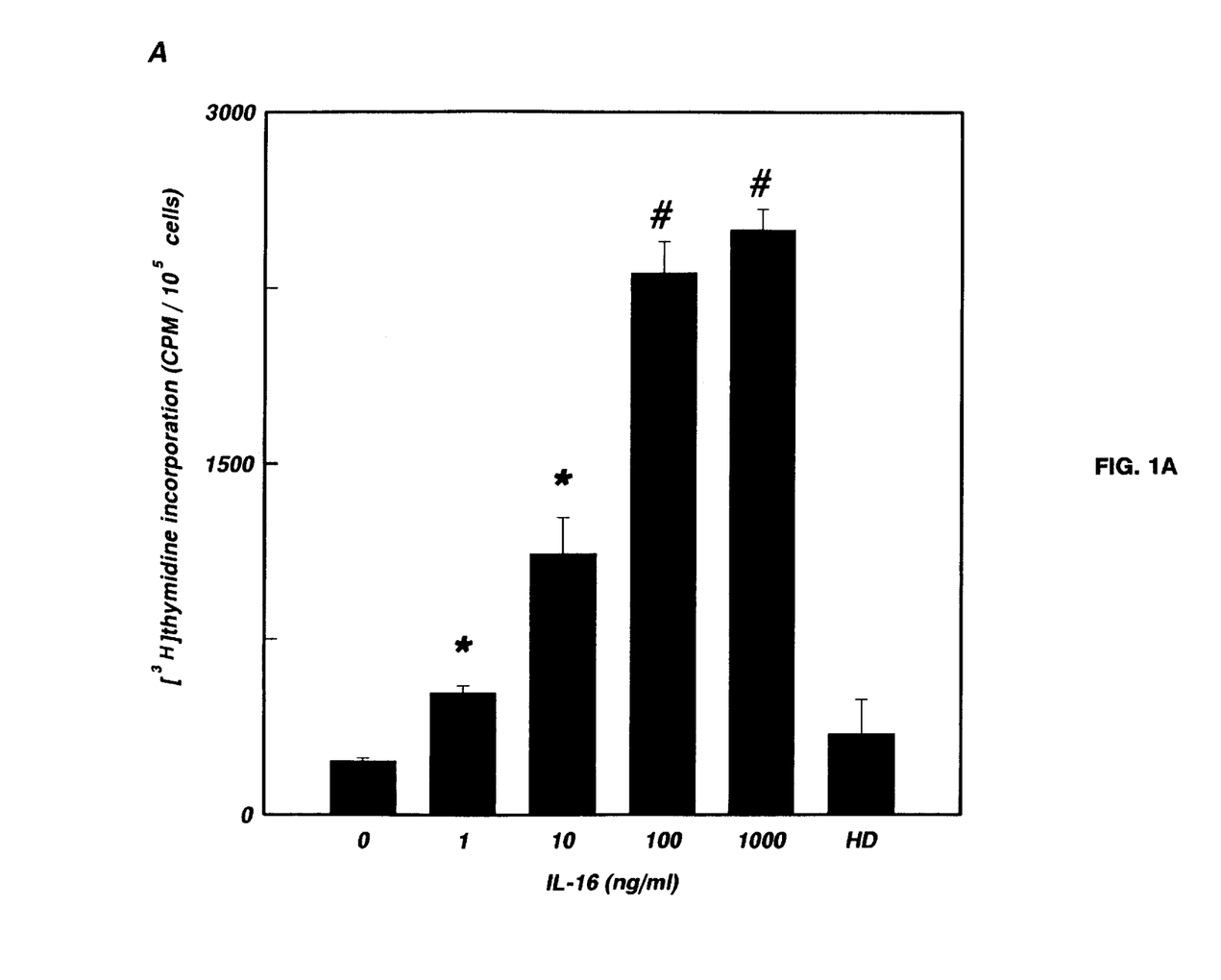
FIGS. 1A and B are diagrams of [$^3$H] thymidine incorporation in PBL cells versus various concentrations of IL-16 (A) and IL-16 and antibody (B).

FIG. 1A diagrams PBLs cultured with varying doses of purified recombinant human IL-16, or heat denatured (HD) IL-16 (1000 ng/ml). [$^3$H]-TdR incorporation is measured after 72 hours. The symbol * indicates that p<0.02. The symbol # indicates that p<0.01. FIG. 1A shows that IL-16 increased [$^3$H]-TdR incorporation in these cultures with significant proliferation observed at 1 ng/ml (58 pM).

From the data presented in FIG. 1A, a $K_d$ of 865±193 pM was calculated, where the $k_d$ represents the amount of IL-16 required to elicit 50% of the maximum biological response.

Figure 1B:
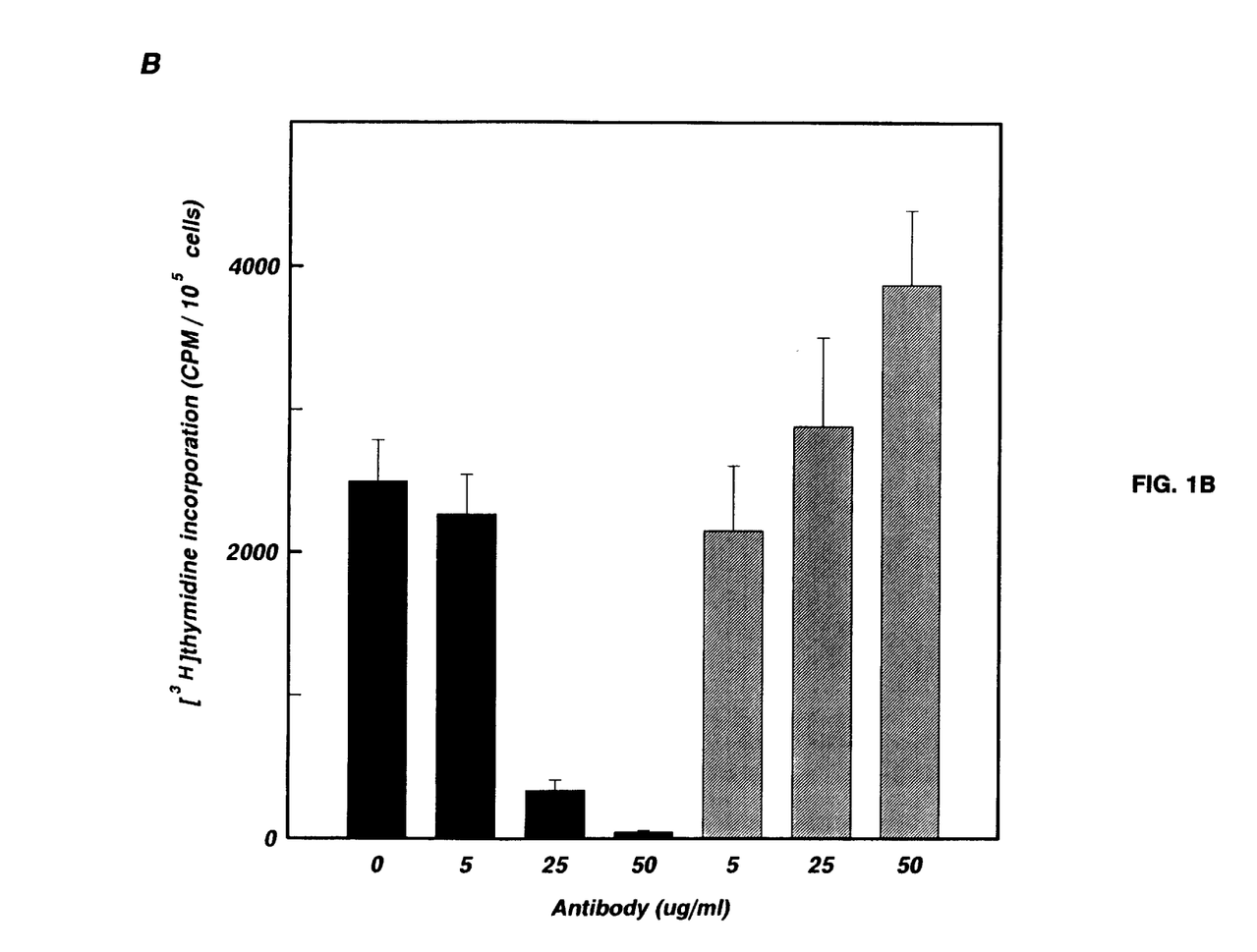

To demonstrate specificity, we determined the activity of recombinant IL-16 after heat denaturation and treatment with a neutralizing antiserum raised against native IL-16 (E. Knight, Jr., et al., *J. Biol. Chem.* 263:4520, 1988). Both heat denaturation and addition of IL-16-specific IgG reduced the activity to the baseline level (FIG. 1A and 1B). FIG. 1B demonstrates the specificity of the proliferative response of PBLs in the presence of human recombinant IL-16 (100 ng/ml) with varying doses of an IgG fraction of a polyclonal rabbit antibody to native IL-16 (solid bars) or normal rabbit serum (stippled bars) (Sigma, St. Louis, Mo.). Proliferation was assessed by [$^3$H]thymidine incorporation, as in FIG. 1A. The baseline proliferation was 34±1.9 CPM.

To more fully define the stimulatory response to PBL cultures to IL-16, we examined the kinetics of the proliferative response. PBLs were incubated with or without recombinant IL-16 for various periods of time and radiolabeled for 12 hours with [$^3$H]thymidine. The PBLs demonstrated a proliferative response to IL-16 that peaked at day 7 while the proliferative response to IL-2 peaked at 5.5 days (FIG. 2).

Figure 2:
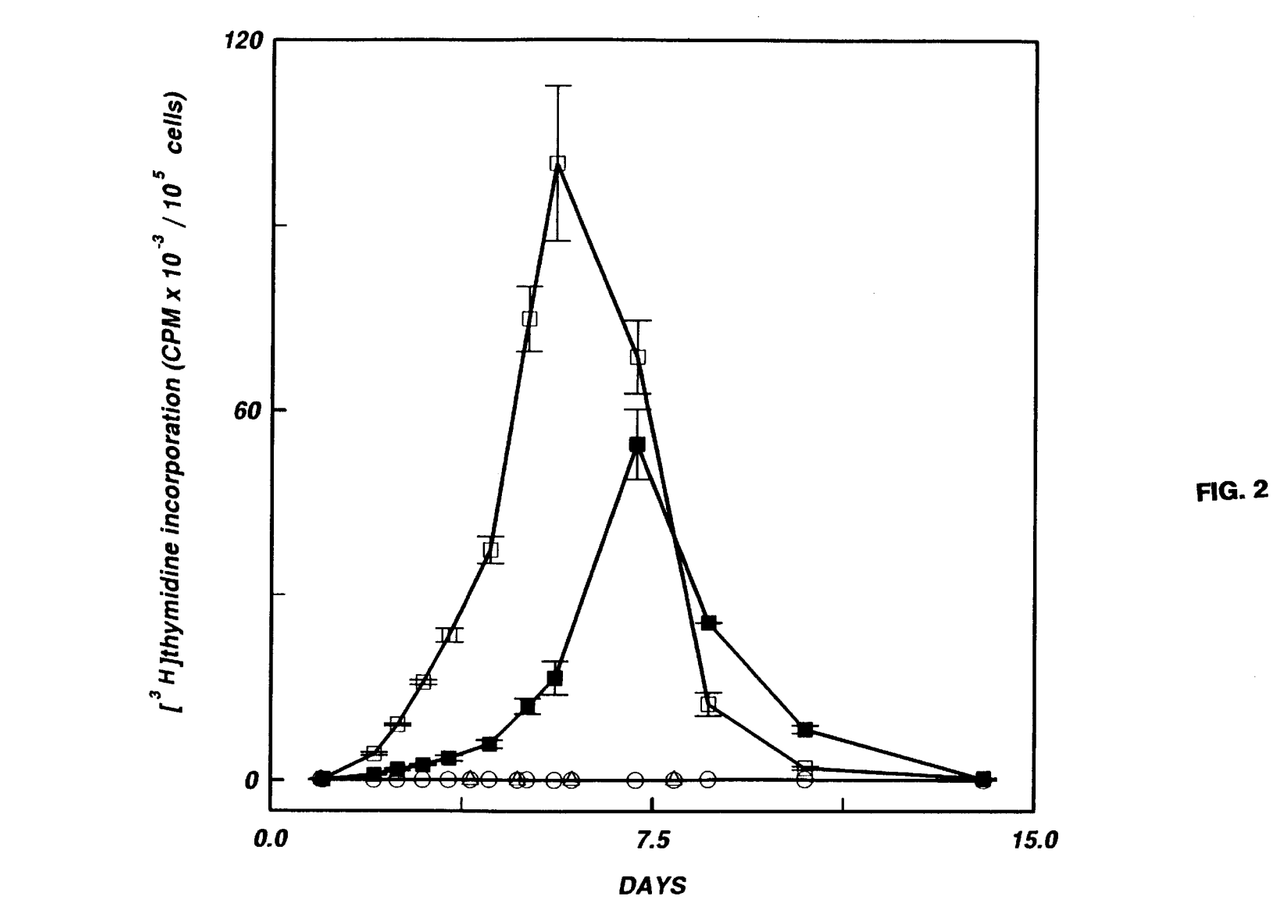
FIG. 2 diagrams the kinetics of the proliferative response of PBLs to IL-16, pre-IL-16, and IL-2.

In FIG. 2 the proliferative response of PBLs to IL-16 (100 ng/ml) (■) was compared to recombinant human pre-IL-16 (1000 ng/ml) (Δ), human recombinant IL-2 (100 U/ml) (Hoffmann-LaRoche, Inc., Nutley, N.J. (□), and medium (○). Proliferation was assessed by 12-hour [$^3$H]-TdR incorporation. Thus, IL-16 appeared to either act on a different population of cells than IL-2 or act through intermediary molecules.

Since the biological significance of the intracellular precursor of IL-16 is not known, we also assessed the ability of human recombinant pre-IL-16 to induce PBL proliferation. There was no enhancement of [$^3$H]-TdR incorporation over that of the control in response to pre-IL-16 (1000 ng/ml) (FIG. 2). The lack of biological activity of pre-IL-16 suggests that removal of the eight carboxyl-terminal amino acids from pre-IL-16 may be important for interactions between IL-16 and its receptor. Alternatively, the processing of pre-IL-16 may be essential in mediating the correct folding of IL-16 to its native conformation. However, the converting enzyme was shown to correctly process recombinant pre-IL-16 to mature IL-16, suggesting that the recombinant precursor was correctly folded into its native conformation.

We analyzed the PBL cultures by flow cytometry at various times after addition of IL-16 in order to identify the phenotype of the responding cells. Comparison of forward versus side-scatter histograms indicated an increased number of large granular lymphocytes in response to IL-16. Staining with fluorescent-conjugated monoclonal antibodies (mAbs) to various cell surface markers identified an increase in the percentage of CD16$^+$cells and a concomitant decrease in the percentage of CD3$^+$cells in the cultures (Table 1A and 1B below). When correlated with cell number, IL-16 induced a 30-fold increase in the number of CD16$^+$cells as compared to the control at 8.5 days of culture. The number of CD3$^+$cells in IL-16-treated cultures remained similar to untreated cultures and there was no change in the numbers of CD4$^+$and CD8$^+$subsets. This indicated that CD3$^+$cells were not proliferating in response to IL-16.

Table 1, below, tabulates IL-16-induced proliferation of CD16$^+$cells in PBL cultures. PBLs were treated with medium (A) or human recombinant IL-16 (100 ng/ml) (B). At various timepoints, cells were removed from culture, counted, and two-color direct immunofluorescence performed as described above. The percent of positive cells are reported as mean percentage ± SEM of duplicate staining reactions after gating on lymphocytes.

Grimm, et al., *J. Exp. Med.* 158:1356, 1983). Both NK and LAK cells lyse targets without the requirement for MHC restriction, and their respective lytic activities are characterized by differential killing of the tumor cell lines K562, an NK-sensitive, LAK-sensitive human erythroleukemic cell line, and Daudi, an NK-resistant, LAK-sensitive Burkitt's lymphoma cell line (R. L. Truitt, et al., *J. Immunotherapy* 11:274, 1992).

Figure 3:
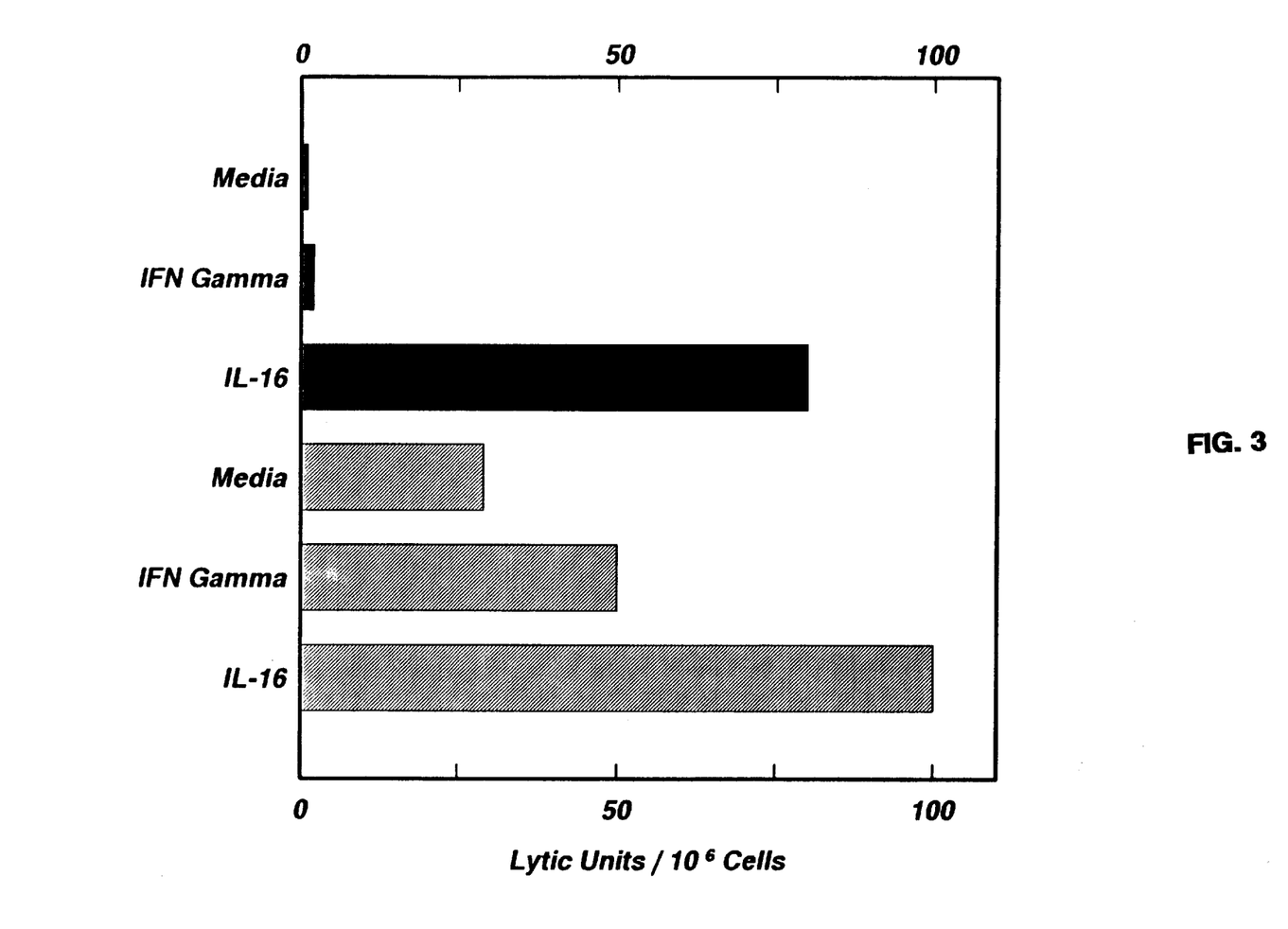
FIG. 3 diagrams NK/LAK cell cytolytic activation by various compounds.

To measure NK/LAK cell cytolytic activity, PBLs were incubated for 4 days with or without IL-16 and co-cultured with $^{51}$Cr-labeled target (Daudi or K562) cells. Activation of PBL with IL-16 resulted in significant induction of LAK-like activity inducing 80 lytic units (LU)/$10^6$ cells against Daudi targets (FIG. 3). IL-16-activated PBL also displayed increased lytic activity (100 LU/$10^6$ cells) against K562 targets attributed to increased LAK-like activity.

In the FIG. 3 experiment, PBLs were cultured for 4 days with medium, IL-16 (100 ng/ml), or IFN-γ ($10^3$ U/ml) (Biogen, Inc., Cambridge, Mass.). Cytolytic activity (percent specific $^{51}$Cr release) in the cultures was quantitated against $^{51}$Cr-labeled Daudi tumor targets (solid bars) or K562 tumor targets (stippled bars). Cytolytic activity (LU/$10^6$ cells) against tumor targets was calculated with one lytic unit defined as the number of responding cells required to generate 30% of maximum $^{51}$Cr release. The data shown represent the means of triplicate determinations.

A number of cytokines, either alone or in combination with other cytokines, have been reported to induce or augment the activity of human LAK cells. Both IL-2 and IL-12, in addition to their ability to induce LAK activity, induce the synthesis of IFN-γ from T cells and NK cells (T. Kashahara, et al., *J. Immunol.* 130:1784, 1983; Kl Handa, et al., *J. Immunol.* 130:988, 1983; M. Kobayashi, et al., *J. Exp.*

TABLE 1

|  | DAY 4 | | DAY 7 | | DAY 8.5 | |
| --- | --- | --- | --- | --- | --- | --- |
| A. Medium | | | | | | |
| Total Cells # (× $10^6$) | 0.91 | | 0.81 | | 0.62 | |
| Cell Surface Marker | CD3$^+$ | CD16$^+$ | CD3$^+$ | CD16$^+$ | CD3$^+$ | CD16$^+$ |
| % Positive Cells | 89 ± 0.1 | 5.9 ± 0.8 | 84 ± 0.1 | 8.8 ± 3.2 | 90 ± 0.1 | 6.2 ± 0.1 |
| Cell Number (× $10^6$) | 0.81 | 0.05 | 0.68 | 0.07 | 0.56 | 0.04 |
| B. IL-16 | | | | | | |
| Total Cells # (× $10^6$) | 0.91 | | 1.14 | | 2.02 | |
| Cell Surface Marker | CD3$^+$ | CD16$^+$ | CD3$^+$ | CD16$^+$ | CD3$^+$ | CD16$^+$ |
| % Positive Cells | 91 ± 0.3 | 4.2 ± 0.7 | 52 ± 0.1 | 43 ± 0.2 | 36 ± 3.4 | 55 ± 1.1 |
| Cell Number (× $10^6$) | 0.83 | 0.04 | 0.67 | 0.49 | 0.73 | 1.11 |

Total Cells refers to the number of cells in 1 ml of culture.

Identification of the proliferation of a CD16$^+$population led us to examine whether IL-16 induced cytokine-dependent, non-MHC restricted cytotoxicity similar to that of IL-2-activated NK cells. NK cells are phenotypically characterized by the surface expression of low affinity receptors for IgG (Fcγ RIII or CD16) (D. Kraft, et al., *J. Immunol.* 133:180, 1984) and by the NCAM-homologous CD56 molecules (L. L. Lanier, et al., *J. Immunol.* 136:4480, 1986). Stimulation of NK cells with IL-2 and certain other lymphokines increases their cytolytic activity and induces the formation of potent effector cells termed lymphokine-activated killer (LAK) cells (G. Trinchieri, *Adv. Immunol.* 47:187, 1989; E. A. Grimm, et al., *J. Exp. Med.* 155:1823, 1982; E. A. Grimm, et al., *J. Exp. Med.* 157:884, 1983; E. A.

*Med.* 170:827, 1989; S. F. Wolf, et al., *J. Immunol.* 146:3074, 1991; S. H. Chan, et al., *J. Exp. Med.* 173:869, 1991. IL-2 and IL-12 share several activities with IL-16, but not IL-2 or IL-12 was detected by ELISA is response to IL-16 (Table 2).

Table 2 demonstrates that IL-16 induced IFN-γ, but not IL-2 and IL-12 in PBL supernatants. PBLs were cultured ($10^7$ cells/ml) with or without IL-16 (100 ng/ml) and cell-free supernatants assayed using commercially available kits for the presence of IFN-γ by radioimmunoassay (Centacor Corp., Malvern, Pa.) or IL-2 (sensitivity of 6 pg/ml) and IL-12 (sensitivity of 5 pg/ml) by ELISA (R&D Systems Inc., Minneapolis, Minn.).

TABLE 2

| Treatment | Cytokine measured | Culture time (hours) | | | |
|---|---|---|---|---|---|
| | | 12 | 25.5 | 48 | 72 |
| Medium | IFN-γ (U/ml) | <1 | <1 | <1 | <1 |
| | IL-2 (pg/ml) | <5 | <5 | <5 | <5 |
| | IL-12 (pg/ml) | <6 | <6 | <6 | <6 |
| IL-16 | IFN-γ (U/ml) | 107 | 435 | 735 | 507 |
| | IL-2 (pg/ml) | <5 | <5 | <5 | <5 |
| | IL-12 (pg/ml) | <6 | <6 | <6 | <6 |

In PBL cultures, there was a maximum accumulation of IFN-γ 48 hours after the addition of IL-16 with levels in excess of 700 U/ml (Table 2). To identify which cell type was producing IFN-γ in response to IL-16, CD3+cells were separated from CD56+cells and treated with IL-16. Reverse-transcriptase PCR (RT-PCR) with IFN-γ-specific primers demonstrated the induction of IFN-γ mRNA in PBLs (CD3+ and CD56+mixed populations) and in purified CD3+cells cultured with IL-16 . Purified CD56+cells, however, did not produce IFN-γ mRNA after addition of IL-16. IL-16 induced high levels of IFN-γ from T cells but not NK cells when the populations were treated independently. In this experiment, after 18 hours of culture with or without IL-16 (100 ng/ml), total RNA was isolated and RT-PCR performed with IFN-γ-specific primers. PCR reactions were precipitated, separated by 1.5% agarose gel electrophoresis, and visualized by ethidium bromide staining. Expected length of amplified PCR product representing IFN-γ MRNA is 427 bp. The electrophoretic lanes we analyzed were as follows: M, Φ X174/Haelll digest; 1, Untreated PBLs; 2, IL-16-treated PBLs; 3, Untreated CD3+cells; 4, IL-16-treated CD3+cells; 5, Untreated CD56+cells; 5, IL-16-treated CD56+cells. Only lane 4 produced the 427 bp band.

Proliferation of CD16+cells and potent induction of LAK cell activity by IL-16 was not the result of IFN-γ production alone from CD3+cells, since recombinant IFN-γ ($10^3$ U/ml) failed to induce PBL proliferation and only modestly enhanced the induction of LAK-like activity (2 LU/$10^6$ cells).

Although IL-16 has no homology to any known secreted protein or cytokine, it has significant amino acid sequence homology with ubiquitin, an 8.6-kDa protein which is covalently ligated via its carboxyl-terminus to intracellular proteins, thereby targeting them for degradation (Loeb and Haas, *J. Biol. Chem.* 267:7806, 1992; Hershko, et al., *Proc. Natl. Acad. Sci.* 77:1783, 1980; Hershko and Ciechanover *Ann. Rev. Biochem.* 61:761,1992). Interestingly, early investigations into the biological function of ubiquitin identified it as a molecule that induced the differentiation of T lymphocytes and B lymphocytes. In our system, ubiquitin did not enhance [+H]-TdR incorporation when cultured with PBLs for up to 10 days. Since ubiquitin is not a secreted protein, the lymphocyte differentiation properties attributed to ubiquitin may have been due to biologically active IL-16.

3. Discussion

IL-16 may represent an important mediator of the immune response to intracellular bacteria and viruses. In response to viral infection, IFN-α or IFN-β are induced and subsequently activate gene expression of pre-IL-16. Importantly, the secretion of IL-16 in response to IFN-α and IFN-β has been identified in a wide variety of cell types. Once secreted or upon lysis of the virally infected cell, IL-16 can induce CD3+cells to produce IFN-γ and activate NK-derived LAK cells. In both human and murine systems, in vitro production of IFN-γ directs the development of CD4+cells to the $T_H1$ phenotype (Gajewski, et al., *J. Immunol.*, 140:4245, 1988; Magge, et al., *J. Immunol.*, 148:2142, 1992). The differentiation of CD4+cells into the $T_H1$ phenotype has been proposed to be a critical step for mediating cellular immunity to viruses and intracellular bacteria (S. Romagnani, *Immunol. Today* 13:379, 1992). In contrast to IL-2 and IL-12, IL-16 induces IFN-γ in T cells and not NK cells, thus yielding a potential cellular specificity in the immune response to intracellular pathogens.

The cytokine network is comprised of many molecules with overlapping and complementary functions. The in vivo role of each molecule is likely linked to specific steps in immunological activation. IL-2 and IL-12 are important participants in regulating T and NK cell responses. However, there molecules, for the requirement of additional molecules, one of which is IL-16. Understanding the biological activities of IL-16 will aid in dissecting host response to viral infection and neoplasia, probing interactions with other cytokines, and lead to use of IL-16 as an immunotherapeutic agent.

We claim:

1. A method for proliferating natural killer cells in vitro comprising culturing lymphocytes which contain natural killer cells in the presence of an effective amount of IL-16 to stimulate proliferation of said natural killer cells, proliferating said natural killer cells, and isolating the proliferated natural killer cells.

2. The method of claim 1 wherein the IL-16 has the amino acid sequence disclosed in SEQ ID NO:1 minus the final 8 amino acids at the carboxy terminus.

3. The method of claim 1 wherein the effective amount of IL-16 is at a concentration of between 1 ng/ml and 1000 ng/ml.

4. The method of claim 1 wherein the effective amount of IL-16 is at a concentration of between 50 ng/ml and 500 ng/ml.

5. The method of claim 1 wherein the IL-16 is in a liquid carrier.

6. The method of claim 1 wherein the natural killer cells are proliferated at least 5 fold.

7. The method of claim 1 wherein the natural killer cells are proliferated at least 13 fold.

8. The method of claim 1 wherein the culturing is for at least 4 days.

9. The method of claim 1 wherein the culturing is for at least 7 days.

10. The method of claim 1 wherein the lymphocytes are nylon wool purified.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 165 amino acids
      (B) TYPE: amino acid
      (C) STRANDEDNESS: single
      (D) TOPOLOGY: linear    (ii) MOLECULE TYPE: protein    (xi) SEQUENCE DESCRIPTION: SEQ ID NO:1:

```
Met Gly Trp Asp Leu Thr Val Lys Met Leu Ala Gly Asn Glu Phe Gln
1               5                   10                  15

Val Ser Leu Ser Ser Ser Met Ser Val Ser Glu Leu Lys Ala Gln Ile
            20                  25                  30
```

```
Thr Gln Lys Ile Gly Val His Ala Phe Gln Gln Arg Leu Ala Val His
        35              40                  45
Pro Ser Gly Val Ala Leu Gln Asp Arg Val Pro Leu Ala Ser Gln Gly
        50              55                  60
Leu Gly Pro Gly Ser Thr Val Leu Leu Val Val Asp Lys Cys Asp Glu
65                      70              75                  80
Pro Leu Ser Ile Leu Val Arg Asn Asn Lys Gly Arg Ser Ser Thr Tyr
                85                  90                  95
Glu Val Arg Leu Thr Gln Thr Val Ala His Leu Lys Gln Gln Val Ser
            100             105                 110
Gly Leu Glu Gly Val Gln Asp Asp Leu Phe Trp Leu Thr Phe Glu Gly
        115                 120                 125
Lys Pro Leu Glu Asp Gln Leu Pro Leu Gly Glu Tyr Gly Leu Lys Pro
        130             135                 140
Leu Ser Thr Val Phe Met Asn Leu Arg Leu Arg Gly Gly Gly Thr Glu
145                     150             155                 160
Pro Gly Gly Arg Ser
                165
```